US007514545B2

(12) United States Patent
Fandl et al.

(10) Patent No.: US 7,514,545 B2
(45) Date of Patent: *Apr. 7, 2009

(54) INDUCIBLE EUKARYOTIC EXPRESSION SYSTEM

(75) Inventors: James P. Fandl, LaGrangeville, NY (US); Changlin Dou, Redwood City, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/332,431

(22) Filed: Jan. 13, 2006

(65) Prior Publication Data

US 2006/0107341 A1 May 18, 2006

Related U.S. Application Data

(63) Continuation of application No. 10/447,243, filed on May 28, 2003.

(60) Provisional application No. 60/384,004, filed on May 29, 2002.

(51) Int. Cl.
*C07H 21/04* (2006.01)
*C12N 5/00* (2006.01)
*C12N 5/06* (2006.01)
*C12N 5/08* (2006.01)
*C12P 21/00* (2006.01)

(52) U.S. Cl. ............... 536/23.4; 435/325; 435/365; 435/358; 435/369; 435/69.1; 435/70.1; 435/70.3; 435/91.1; 435/91.3; 536/23.5

(58) Field of Classification Search ............... None
See application file for complete search history.

(56) References Cited

U.S. PATENT DOCUMENTS

| | | | |
|---|---|---|---|
| 4,833,080 | A | 5/1989 | Brent et al. |
| 5,599,904 | A | 2/1997 | Evans et al. |
| 5,739,018 | A | 4/1998 | Miyanohara et al. |
| 5,756,448 | A | 5/1998 | Moore et al. |
| 5,972,650 | A * | 10/1999 | Yao ............... 435/69.1 |
| 6,117,680 | A | 9/2000 | Natesan et al. |
| 6,183,965 | B1 | 2/2001 | Verdine et al. |
| 6,271,348 | B1 | 8/2001 | Bujard et al. |
| 6,432,705 | B1 | 8/2002 | Yee et al. |
| 7,112,715 | B2 | 9/2006 | Chambon et al. |
| 7,153,685 | B2 | 12/2006 | Mao et al. |
| 2002/0115629 | A1* | 8/2002 | Ramachandra ......... 514/44 |
| 2003/0186841 | A1 | 10/2003 | Barbas et al. |
| 2004/0102367 | A1* | 5/2004 | Gage et al. ............ 514/12 |

FOREIGN PATENT DOCUMENTS

WO    WO01/30843 A    5/2001

OTHER PUBLICATIONS

Wang et al. Positive and negative regulation of gene expression in eukaryotic cells with an inducible transcriptional regulator. Gene Therapy (1997), vol. 4, pp. 432-441.*
Kumar et al. (1999) Steriods 64:310-319.*
Lee et al. (1994) Mol. Endocrinol. 8:1245-1252.*
Richards (1997) Cell Mol. Life Sci. 53:790-802.*
Sun et al. (2000) Mol. Biochem. Parisitol. 105:51-6.*
Littlewood et al. (1995) Nucl. Acids Res. 23:1686-1690.*
Feil et al. (1997) Biochem. Biophys. Res. Commun. 237:752-757.*
Deuschle, et al., (1995) Mol. Cell. Biology 15(4):1907-1914.
No, et al., (1996) Proc. Natl. Acad. Sci. USA 93:3346-3351.
Iida, et al., (1996) J. Virology 70(9):6054-6059.
Mattioni, et al., (1994) Methods in Cell Biology 43:335-352.
Feil, R. et al. (1997) Regulation of Cre Recobminase Activity by Mutated Estrogen Receptor Ligand-Binding Domains, Biochem. Biophys. Res. Commun. 237:752-757.
Gossen, M. et al. (1992) Tight control of gene expression in mammalian cells by tetracycline-responsive promoters, Proc. Natl. Acad. Sci., USA 89:5547-5551.
Knight, K. et al. (1989) The Arc and Mnt Repressors: A new Class of Sequence-Specific DNA-Binding Protein, J. Biol. Chem. 264/7:3639-3642.
Littlewood, T. et al. (1995) A modified oestrogen receptor ligand-binding domain as an improved switch for the regulation of . . . , Nucleic Acids Res. 23/10:1686-1690.
Ma, Z. et al. (1999) Suppression of gene expression by tethering KRAB domain to promoter of ER target genes, J. Steroid Biochem. Mol. Biol. 69:155-163.
Robinson, C. et al. (1998) Optimizing the stability of single-chain proteins by linker length and composition mutagenesis, Proc. Natl. Acad. Sci. USA 95:5929-5934.
Smith, T. et al. (1996) Dual regulation of open-complex formation and promoter clearance by Arc explains a novel repressor . . . , Proc. Natl. Acad. Sci. USA. 93:8868-8872.
Sun, C. et al. (2000) Development of tetracycline controlled gene expression system in parasistic protozoan . . . , Mol. Biochem. Parasit. 105:51-60.
Golemis, A. et al. (1992) Fused Protein Domains Inhibit DNA Binding by LexA, Mol. & Cell. Biol. 12/7: 3006-3014.

* cited by examiner

*Primary Examiner*—Daniel M Sullivan
(74) *Attorney, Agent, or Firm*—Tor Smeland, Esq.; Valeta Gregg, Esq.

(57) ABSTRACT

Compositions and methods for the inducible expression of genes in eukaryotic cells. Expression of a nucleotide sequence of interest is controlled by a regulatory fusion protein that consists of a transcription blocking domain and a ligand-binding domain. When the cognate ligand for the ligand-binding domain is present, transcription of the nucleotide sequence of interest is blocked. Upon removal of the cognate ligand, the nucleotide sequence of interest is transcribed. The method is useful for large scale production of a desired product in eukaryotic cells.

5 Claims, 7 Drawing Sheets

FIG. 6.

```
                    arcO                           arcO
TATAAGCAGAGCTCATGATAGAATCACTCTACTATTCATGATAGAAGCACTCTACTAT
ATATTCGTCTCGAGTACTATCTTAGTGAGATGATAAGTACTATCTTCGTGAGATGATA
```

INDUCIBLE EUKARYOTIC EXPRESSION SYSTEM

STATEMENT OF RELATED PATENT APPLICATIONS

This application is a continuation application of prior U.S. application Ser. No. 10/447,243 filed 28 May 2003, which claims benefit under 35 USC § 119(e) of U.S. Provisional Application No. 60/384,004, filed 29 May 2002, which applications are herein specifically incorporated by reference in their entirety.

FIELD OF THE INVENTION

The present invention relates to methods for the inducible expression of genes in eukaryotic cells. The invention further includes cells capable of inducible gene expression, transgenic animals comprising such cells, and nucleotide sequences and proteins comprising regulatory fusion proteins.

BACKGROUND OF TH INVENTION

Various methods for controlled expression of a recombinant nucleotide sequence of interest in a cell are known to the art. For example, No et al. (1996) Proc. Natl. Acad. Sci. USA 93:3346-3351, describe an inducible gene expression system utilizing a chimeric transactivator consisting of the ecdysone nuclear receptor fused to the VP16 transactivation domain. In the presence of inducer, this chimeric transactivator binds to recognition sequences upstream from a promoter and stimulates transcription of a nucleotide sequence of interest. In the absence of inducer, expression of the nucleotide sequence of interest is reduced and dependent on the basal level of transcription from the nucleotide sequence of interest promoter. Gossen et al. (1992) Proc. Natl. Acad. Sci. USA 89:5547-5551, describe a system for regulating expression of a nucleotide sequence of interest based on a chimeric protein, tTA, consisting of the TetR repressor protein fused with the VP16 transactivation domain. Similar to the ecdysone system, the DNA sequences specifying the TetR DNA binding site are inserted upstream of the gene promoter such that binding of the TetR-VP16 fusion protein stimulates transcription from the promoter and expression of the nucleotide sequence of interest. Other systems targeted to specific DNA binding sites proximal to a minimal promoter for targeted regulation of transcription utilizing the VP16 transactivation domain have also been developed, including GAL4-VP16 (Sadowski et al. (1988) Nature 335:563-564), LexA-VP16 (Brent et al. (1985) Cell 40:729-736), and LacI-VP16 (Labow et al. (1990) Mol. Cell. Biol. 10:3342-3356). Other TetR-based systems are described in Deuschle et al. (1995) Mol. Cell. Biol. 15:1907-1914 and Yao et al. (1998) Hum. Gene Ther. 13:1939-1950.

Problems resulting from leaky expression related to the use of a minimal promoter have led to systems using fusions of the steroid-binding domains of the glucocorticoid or estrogen nuclear receptors (see, for example, Mattioni et al. (1994) Methods Cell Biol. 43:335-352; Louvion et al. (1993) Gene 131:129-134; Iida et al. (1996) J. Virol. 70: 6054-6059.

BRIEF SUMMARY OF THE INVENTION

The present invention is directed to a tightly regulated inducible gene expression system suitable for large scale production of a recombinant molecule of interest in a eukaryotic cell. The components of the system of the instant invention include a fusion protein having a transcription blocking domain and a ligand-binding domain; an operator which binds the transcription blocking domain of the fusion protein to inhibit transcription of a nucleotide sequence; and a promoter which is under the control of the operator. When expression of the nucleotide sequence of interest is desired to be inhibited, the system includes a ligand which is capable of binding the ligand-binding domain of the fusion protein, such that the fusion protein is stabilized. When it is desired that the nucleotide sequence of interest be expressed, the ligand is removed, which results in destabilization and degradation of the fusion protein. Accordingly, in the absence of the cognate ligand, the fusion protein is removed from the operator, and operator-inhibition of the promoter controlling expression of the nucleotide sequence of interest is removed, thereby allowing the nucleotide sequence of interest to be expressed.

In a first aspect, the invention provides a method of inducing expression of a nucleotide sequence of interest in a eukaryotic cell comprising (a) providing a eukaryotic cell comprising (i) a nucleotide sequence encoding a regulatory fusion protein (RPR), wherein the fusion protein consists of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein; and (iii) an operator capable of binding the transcription blocking domain and blocking transcription from the adjacent promoter; (b) growing the cell of step (a) to a desired density in the presence of a ligand which binds the ligand-binding domain of the fusion protein, wherein expression of the nucleotide sequence of interest is inhibited; and (c) removing the ligand from the presence of the cell, wherein expression of the nucleotide sequence of interest is induced.

The transcription blocking domain is a protein capable of binding DNA and blocking transcription from an adjacent promoter. In more specific embodiment, the transcription blocking domain may be derived from a bacterial, bacteriophage, eukaryotic, or yeast repressor protein. In more specific embodiments, the transcription blocking domain is derived from a bacterial or bacteriophage repressor protein. In even more specific embodiments, the transcription blocking domain is derived from a repressor protein selected from the group consisting of TetR, LexA, LacI, TrpR, Arc; and LambdaCl. In another embodiment, the transcription blocking domain is derived from a eukaryotic repressor protein. In an even more specific embodiment, the repressor domain is derived from GAL4.

In another specific embodiment of the method of the invention, the transcription blocking domain is a mutated restriction enzyme capable of binding but not cleaving DNA, and the operator is a recognition site for the restriction enzyme. In a more specific embodiment, the transcription blocking domain is a mutated Not1.

In specific embodiments, the ligand-binding domain is derived from a steroid, thyroid, or retinoid receptor. In more specific embodiments, the ligand-binding domain is derived from an estrogen receptor, and the cognate ligand is an estrogen. In an even more specific embodiment, the estrogen receptor contains one or more mutations, for example, the T2 mutations, and the cognate ligand is tamoxifen.

A variety of eukaryotic cells may be used in the method of the invention, including without limitation, a yeast cell, such as *Pichia pastoris*, or a mammalian cell, such as a COS, CHO, 293, BHK or NS0 cell.

The instant invention may be broadly used in the transcription of a nucleotide sequence of interest, and the product of interest may be the transcription product, e.g., an mRNA or catalytically active RNA, or a downstream product resulting from the transcribed nucleotide sequence of interest, for example, a protein or protein fragment, including without limitation, a hormone, a receptor or receptor fragment, an antibody or antibody fragment, a biologically active peptide or protein, an enzyme, a repressor protein, or a DNA binding protein.

In a second aspect, the invention features an isolated nucleotide sequence encoding a regulatory fusion protein (RPR), wherein the fusion protein consists of (1) a transcription blocking domain capable of inhibiting expression of the nucleotide sequence of interest, and (2) a ligand-binding domain, wherein in the presence of a cognate ligand capable of binding the ligand-binding domain, the fusion protein is stabilized.

In separate embodiments, the transcription blocking domain may be derived from a bacterial, bacteriophage, eukaryotic, or yeast repressor protein. In more specific embodiments, the transcription blocking domain is derived from a bacterial or bacteriophage repressor protein, such as, for example, TetR, LexA, LacI, TrpR, Arc, and LambdaCI. In another embodiment, the transcription blocking domain is derived from a eukaryotic repressor protein, such as, for example, GAL4. In another specific embodiment, the transcription blocking domain is a mutated restriction enzyme capable of binding but not cleaving DNA, and the operator is a recognition site for the restriction enzyme. In this specific embodiment, for example, the transcription blocking domain is a mutated NotI.

In specific embodiments, the ligand-binding domain is derived from a steroid, thyroid, or retinoid receptor. In more specific embodiments, the ligand-binding domain is derived from an estrogen receptor, and the cognate ligand is an estrogen. In an even more specific embodiment, the estrogen receptor contains one or more mutations, for example, the T2 mutations, and the cognate ligand is tamoxifen.

In a third related aspect, the invention features a regulatory fusion protein (RPR) consisting of (1) a transcription blocking domain capable of inhibiting expression of the nucleotide sequence of interest, and (2) a ligand-binding domain, wherein in the presence of a cognate ligand capable of binding the ligand-binding domain, the fusion protein is stabilized. In a specific embodiment, the regulatory fusion protein (RPR) consisting essentially of (1) a transcription blocking domain capable of inhibiting expression of the nucleotide sequence of interest, and (2) a ligand-binding domain, wherein in the presence of a cognate ligand capable of binding the ligand-binding domain, the fusion protein is stabilized.

In a fourth aspect, the invention features a eukaryotic cell capable of inducible expression of a nucleotide sequence of interest, comprising a nucleotide sequence encoding a regulatory fusion protein (RPR), wherein the fusion protein consists of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein, and (iii) an operator capable of binding the transcription blocking domain and blocking transcription from the adjacent promoter. In a specific embodiment, the eukaryotic cell the fusion protein consists essentially of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein, and (iii) an operator capable of binding the transcription blocking domain and blocking transcription from the adjacent promoter.

In a fifth aspect, the invention features a transgenic animal comprising a eukaryotic cell capable of inducible expression of a nucleotide sequence of interest, comprising a nucleotide sequence encoding a regulatory fusion protein (RPR), wherein the fusion protein consists of (1) a transcription blocking domain capable of inhibiting expression of the nucleotide sequence of interest, and (2) a ligand-binding domain; (ii) a promoter operably linked to the nucleotide sequence of interest and controlled by an operator that binds the fusion protein, and (iii) an operator capable of binding the transcription blocking domain and blocking transcription from the adjacent promoter.

Other objects and advantages will become apparent from a review of the ensuing detailed description.

BRIEF DESCRIPTION OF THE FIGURES

FIG. 6 is a schematic diagram of the CMV-MIE/AO hybrid promoter (SEQ ID NO:6, top strand, and SEQ ID NO: 7, bottom strand) having tandem arc operators immediately downstream of the CMV-MIE promoter/enhancer (TATA box).

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

The present invention is based in part on the concept that gene expression in eukaryotic cells can be tightly regulated using a strong promoter that is controlled by an operator that is in turn regulated by a regulatory fusion protein (RFP). The RFP consists essentially of a transcription blocking domain, and a ligand-binding domain that regulates its activity. In the presence of the cognate ligand for the ligand-binding domain, the RFP binds the operator thereby preventing transcription of the GOI. When the cognate ligand is withdrawn, the RFP is destabilized and transcription of the nucleotide sequence of interest proceeds.

Figure 4:
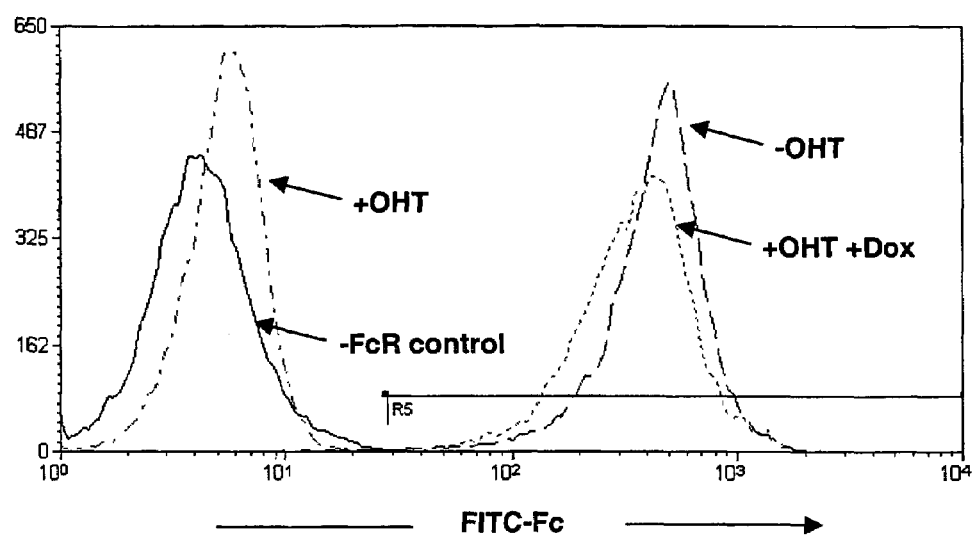
FIG. 4 show flow cytometry histograms of CHO K1-FcR/pTE313 clone D124 grown in the presence or absence of OHT, or in the presence of OHT and Dox, stained with FITC-Fc.
Figure 7:
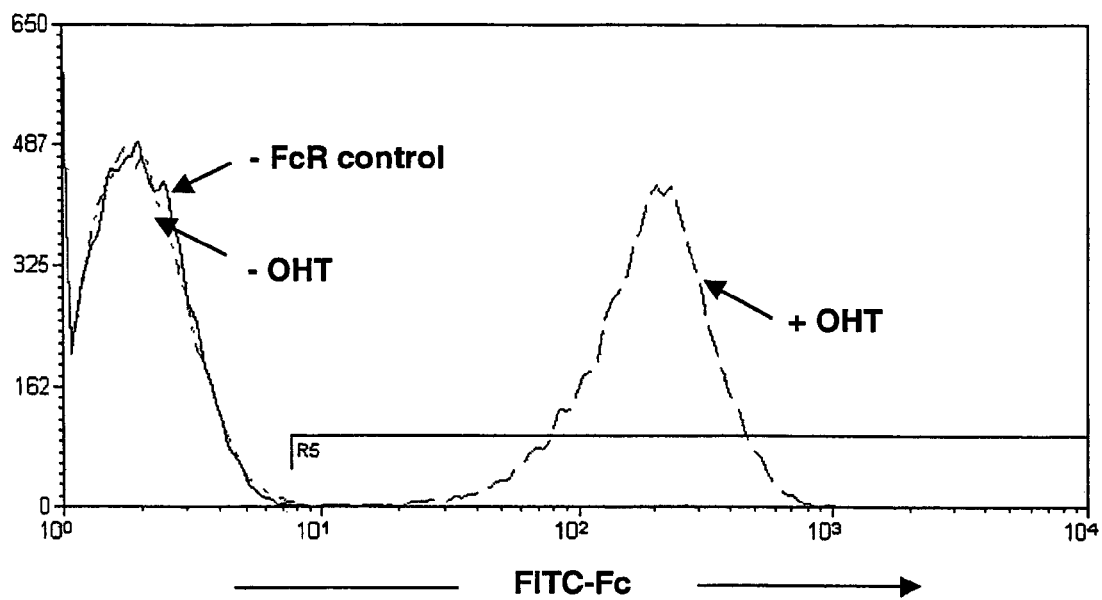
FIG. 7 show flow cytometry histograms of CHO K1-FcR/pTE534 clone C17 grown in the presence or absence of OHT, stained with FITC-Fc.

The regulatory system described herein provides specific advantages which combine a tightly regulated control of expression of a nucleotide sequence of interest with the isolation of cell lines capable of high level expression of the nucleotide sequence of interest suitable for large scale production. The term "tightly regulated" is meant that in the presence of a ligand that binds the ligand binding domain of the fusion protein of the invention, transcription of the nucleotide sequence of interest is substantially reduced, e.g., for example, at least a 20-fold decrease in transcription is achieved in the presence of the ligand relative to the level of transcription seen in the absence of the ligand. In more specific embodiments, the method of the invention achieves at least a 50-fold decrease in transcription in the presence of ligand. In even more specific embodiments, the method of the invention achieves a 100-fold or greater decrease in transcription in the presence of ligand. Examples of the degree of transcription control achieved by the methods of the invention are seen in FIGS. 4 and 7. The degree of regulation of transcription achieved by the method of the invention may also be stated as a difference in the expression of the nucleotide sequence of interest in the absence of the ligand is at least 20-fold greater, preferably at least 50-fold greater, more preferably at least 100-fold greater, than expression of the nucleotide sequence of interest in the presence of the ligand.

Isolation of cell lines capable of expressing a nucleotide sequence of interest at high levels requires tight regulation, but induction of the nucleotide sequence of interest expression is preferably accomplished by removal of an inducer, rather than the addition of one, is of substantial commercial importance as a means of reducing the cost of production relative to a system which requires the addition of a ligand during large-scale production. The present invention describes a regulatory system that satisfies these requirements.

Nucleotide Sequence of Interest

The methods of the invention may be broadly used to control the transcription of any nucleotide sequence of interest. The method of the invention may be used to produce a desired protein or protein fragment, including, for example, fusion and chimeric proteins or peptides. Further, the product of interest may be a transcription product, e.g., an mRNA or catalytically active RNA, or a downstream product resulting from the action of the initial transcription product.

Proteins of interest may include, without limitation, a hormone, a receptor or receptor fragment, an antibody or antibody fragment, a biologically active peptide or protein, an enzyme, a repressor protein, or a DNA binding protein.

Promoters

"Promoter" as used herein indicates a DNA sequence sufficient to direct transcription of a DNA sequence to which it is operably linked, i.e., linked in such a way as to permit transcription of the nucleotide sequence of interest when the appropriate signals are present. The expression of a nucleotide sequence of interest may be placed under control of any promoter or enhancer element known in the art.

Useful promoters which may be used in the invention include, but are not limited to, the SV40 early promoter region, the promoter contained in the 3' long terminal repeat of Rous sarcoma virus, the regulatory sequences of the metallothionein gene, mouse or human cytomegalovirus IE promoter (Gossen et al., (1995) Proc. Nat. Acad. Sci. USA 89:5547-5551); plant expression vectors comprising the nopaline synthetase promoter region, the cauliflower mosaic virus 35S RNA promoter, and the promoter of the photosynthetic enzyme ribulose biphosphate carboxylase; promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I; insulin; immunoglobulin; mouse mammary tumor virus; albumin; α-fetoprotein; α1-antitrypsin; β-globin; and myosin light chain-2.

Operators

As used herein "operator" indicates a DNA sequence that is introduced in or near a gene in such a way that the gene may be regulated by the binding of the RFP to the operator and, as a result, prevent or allow transcription of the GOI. A number of operators in prokaryotic cells and bacteriophage, have been well characterized (Neidhardt, ed. *Escherichia coli and Salmonella*; Cellular and Molecular Biology 2d. Vol 2 ASM Press, Washington D.C. 1996). These include, but are not limited to, the operator region of the LexA gene of *E. coli*, which binds the LexA peptide and the lactose and tryptophan operators, which bind the repressor proteins encoded by the LacI and trpR genes of *E. coli*. These also include the bacteriophage operators from the lambda $P_R$ and the phage P22 ant/mnt genes which bind the repressor proteins encoded by lambda cI and P22 arc. In an alternative embodiment, when the transcription blocking domain of the RFP is a restriction enzyme, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

Transcription blocking Domain

As used herein, a transcription blocking domain is any domain capable of blocking transcription as a result of its interaction with an operator. Such a domain may be derived from bacteria, bacteriophage, or yeast, and includes, but is not limited to, those repressors, or derivatives thereof, whose function depends upon ligand binding, such as TetR, LexA, LacI and Arc. Alternatively, the transcription blocking domain may be derived from mammalian cells as described, for example, in Yin et al. 1995 J. Virol. 69:6209-6218 or plant cells, as described, for example, in Wilde et al. 1994 Plant Mol. Biol. 24:38. The transcription blocking domain may also be made synthetically. For example, the transcription blocking domain may be a restriction enzyme that is mutated such that it can no longer cleave DNA. In such a case, the recognition sequence for that enzyme would be used as the operator.

Ligand-Binding Domain

While the ability of the fusion protein to interact with the operator is controlled by the transcription blocking domain, the activity of the fusion protein is regulated by the ligand-binding domain. The ligand-binding domain can be derived from any polypeptide that, when bound to its cognate ligand, renders the polypeptide functional, including for example, stabilizing the polypeptide. The ligand-binding domain is meant to include naturally occurring ligand-binding domains, as well as functional derivatives thereof. As used herein, "cognate ligand" includes the naturally occurring ligands that bind the ligand-binding domains, as well as functional derivates thereof. Examples of such ligand-binding domains include, but are not limited to, the ligand-binding domains of steroid receptors glucocorticoid receptors, retinoid receptors and thyroid receptors (Eilers et al. (1989) Nature 340:66-68; Picard et al. (1988) Cell 54:1073-1080). Examples 1-3 illustrate one embodiment of the invention, in which the transcription blocking domain of the fusion protein is TetR and the ligand-binding domain is the estrogen receptor ligand-binding domain with T2 mutations ($ER_{LBD}T2$; Feil et al. (1997) Biochem. Biophys. Res. Commun. 237:752-757). When TetO sequences were placed downstream and proximal to the strong CMV-MIE promoter, transcription of the nucleotide sequence of interest (in this case hFcγRI) from the CMV-MIE/TetO promoter was blocked in the presence of tamoxifen and unblocked by removal of tamoxifen.

Cell Selection Methodologies

The methods of the invention produce cells having a high production rate for a nucleotide sequence of interest. In addition to the methods described in the experimental section below, a variety of selection processes known to the art may be used. In one preferred embodiment, the selection process is the "FASTR" methodology described in USSN 20020168702 published 14 Nov. 2002, herein specifically incorporated by reference. The FASTR methodology is a high-throughput screening method for rapid isolation of cells secreting a cytokine-specific fusion protein of the invention, by direct screening of the fusion protein.

Transgenic Animals

The present invention also contemplates the creation of transgenic mammals that express the fusion proteins of the invention. For example, it may be desirable to regulate the expression of nucleotide sequence of interest in a mammal. A gene encoding the fusion proteins of the invention may be integrated into the genome of a mammal so as to regulate the expression of a nucleotide sequence of interest whose promoter was engineered to be responsive to the fusion protein. Further, transgenic animals may be useful as a source of a nucleotide sequence of interest.

A transgenic animal can be produced by introducing a nucleic acid construct into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells.

Kits

The invention also provides a kit comprising one or more containers filled with at least one fusion protein of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

SPECIFIC EMBODIMENTS

Figure 1:
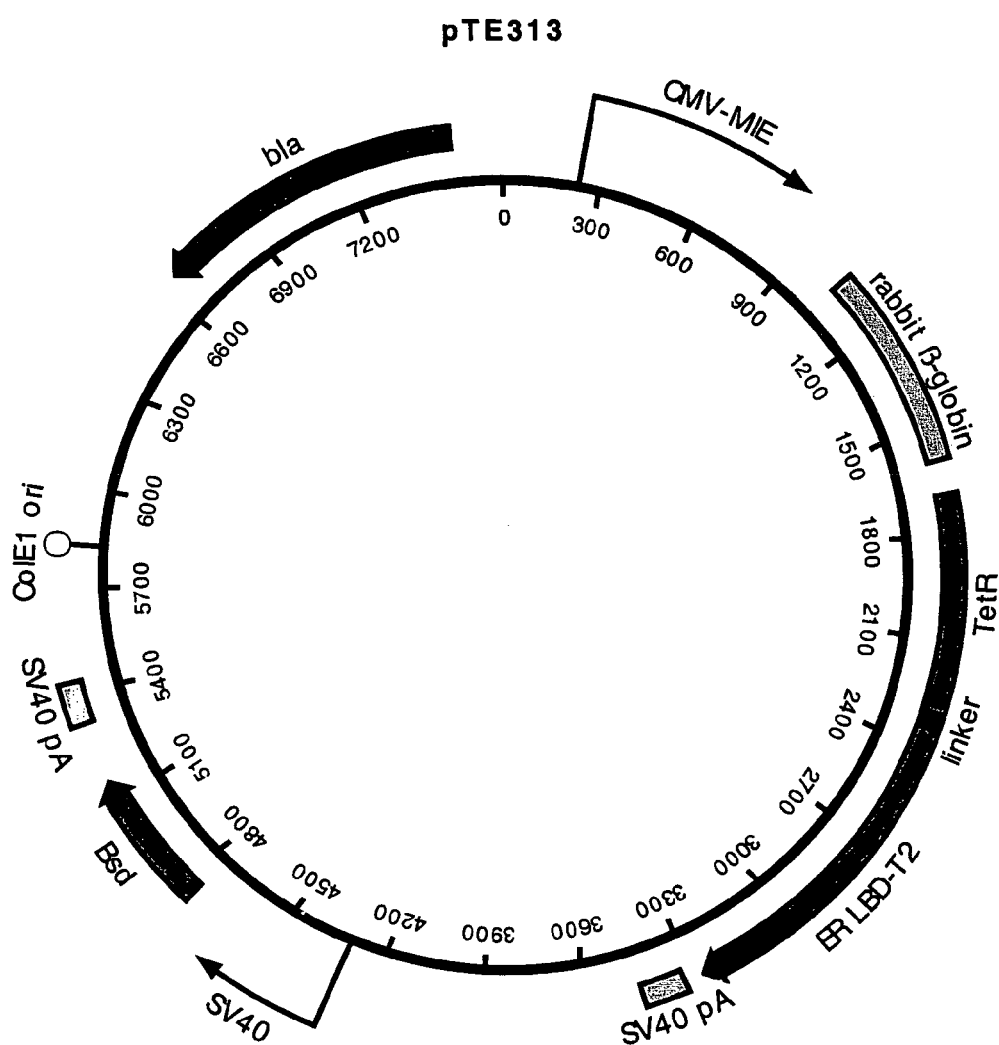
FIG. 1 represents the structure of pTE313, designed for the expression of TetR-ER$_{LBD}$T2 from the CMV promoter.
Figure 2:
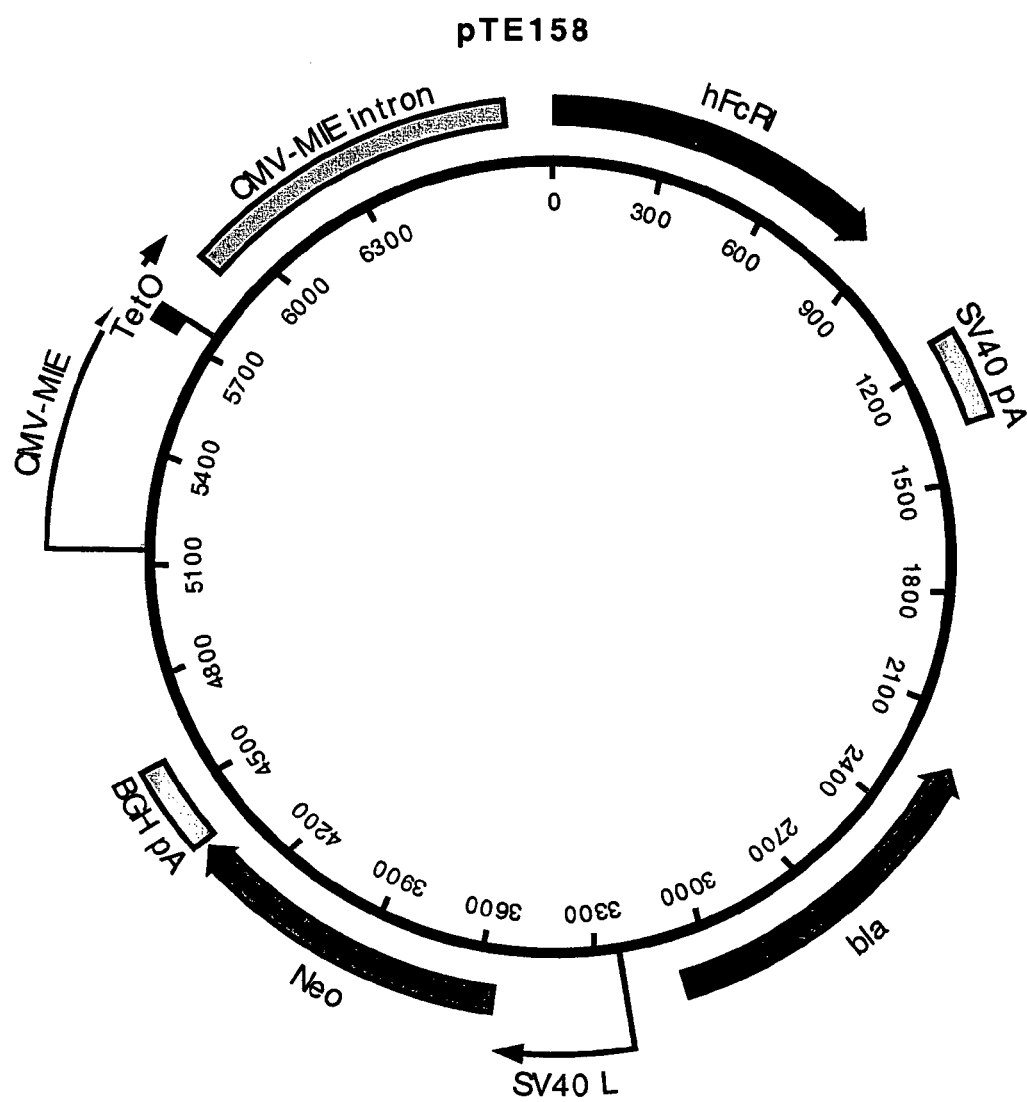
FIG. 2 represents the structure of pTE158, designed for the expression of human FcγRI from a CMV promoter that is regulated by the tetracycline repressor.

Example 1 describes construction of the pTE313, pTE084, and pTE158 plasmids. pTE313 designed for high-level expression of a regulatory fusion protein TetR-$ER_{LBD}T2$. It contains a first independent expression cassette which is the TetR-$ER_{LBD}T2$ fusion gene driven by the CMV-MIE promoter, and the second independent cassette which is the blasticidin resistance gene driven by the SV40 promoter (FIG. 1). pTE084 was designed for the high level expression of hFcγRI, the high affinity cell surface receptor for the Fc domain of human IgG. pTE158 was generated by placing two tandem TetR operator immediately downstream of the CMV-MIE promoter/enhancer in pTE084 (FIG. 2). CHO K1 cells expressing the hFcγRI gene regulated by the TetR-$ER_{LBD}T2$ RFP after transfection with pTE313 were generated and identified as described in Example 2.

Figure 3:
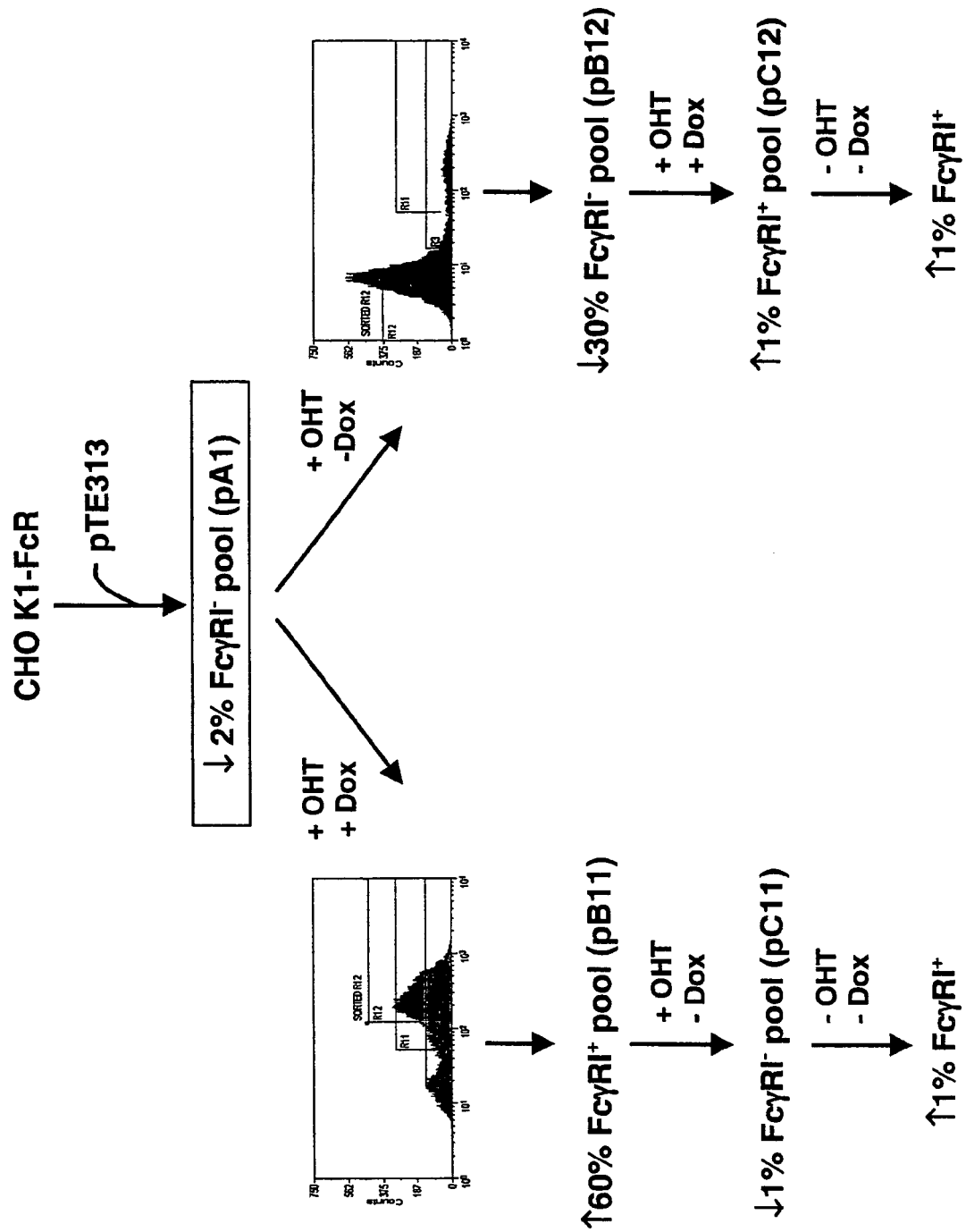
FIG. 3 shows an outline of the two strategies used to isolate CHO K1 clones that expressed the hFcγRI gene regulated by the TetR-ER$_{LBD}$T2 RFP.

Two strategies were employed to isolate clones that expressed the hFcγRI gene regulated by the TetR-$ER_{LBD}T2$ RFP after transfection with pTE313 (FIG. 3). Both strategies started from the same pool of cells obtained after introduction of the TetR-$ER_{LBD}T2$ RFP into CHO K1-FcR cells and isolation (Example 3). These results clearly show that the expression of a recombinant gene can be tightly regulated by TetR-$ER_{LBD}T2$ and induction of expression can be achieved by either the addition of doxycycline in the presence of tamoxifen or the removal of tamoxifen (FIG. 4). Induction of the expression of a nucleotide sequence of interest by removal of a small molecule from the culture medium, easily achieved by dilution or medium exchange, provides a cost-effective means to induce expression at large scale. Moreover, these data show that tight regulation of expression can be achieved by the TetR-$ER_{LBD}T2$ regulatory fusion protein.

CHO K1 cells expressing hFcγRI driven by CMV-MIE/ArcO2 promoter were generated as described in Examples 4 and 5. Inducible cell lines regulated by Arc-$ER_{LBD}T2$ were selected similar to the strategies shown in FIG. 3, and showed tight regulation in response to the presence of OHT in the growth medium (Example 6 and FIG. 7).

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of pTE313, pTE084 and pTE158 pTE313 was constructed by ligating a 975 bp EcoR I fragment (blunted) from pTA-ER-LBD-T2 that encodes the human estrogen receptor ligand binding domain with T2 mutations ($ER_{LBD}T2$) (Feil, et al. 1997 Biochem Biophys Res Commun 237:752-757) into the EcoR I site (blunted, in the linker region immediately following the TetR C-terminus) of pcDNA6/TR (Invitrogen Cat. no. V-1025-20). The T2 mutations G400V, M543A, and L544A confer specificity for binding the estradiol analog tamoxifen. The proper orientation of the fragment encoding $ER_{LBD}T2$ in desirable plasmids resulting from the ligation was confirmed by DNA sequence determination. This construction resulted in a gene encoding a fusion protein consisting of amino acids M1 to S207 of TetR (SEQ ID NO:8) fused to amino acids N304 to V595 of the estrogen receptor (SEQ ID NO:9). The chimeric protein encoded by this gene also has the T2 mutations G400V, M543A, and L544A in the estrogen receptor. Plasmid pTE313 contains a cassette which is the TetR-$ER_{LBD}T2$ fusion gene driven by the CMV-MIE promoter, and a second cassette which is the blasticidin resistance gene driven by the SV40 promoter (FIG. 1).

pTE084 was constructed by ligating the 1,436 bp Xba I fragment from pCAE100 that encodes the human FcγRI (GenBank accession number M21091) into the Xba I site of pRG821, a vector that encodes the neomycin phosphotransferase II (npt) gene which confers resistance to G418. The orientation of hFcgRI in desirable plasmids resulting from the ligation was examined by restriction mapping with Not I, Pst I, Eco RI, and Stu I. A DNA fragment encoding two tandem TetR operators were placed immediately downstream of the CMV-MIE promoter/enhancer in pTE084 to generate pTE158 (FIG. 2). In this plasmid, transcription of hFcγRI from the CMV-MIE promoter was regulated by TetR or TetR-$ER_{LBD}T2$.

Example 2

Construction of a CHO K1 Derivative that Expresses hFcγRI Driven by CMV-MIE/TetO CHO K1 cells ($3 \times 10^6$ cells) were transfected with pTE158 using Lipofectamine™ (Life Technologies; Rockville, Md.) following the manufacturer's suggestions. The cells were placed in the culture medium (10% fetal bovine serum, 90% Ham's F-12, 2 mM L-glutamine; all reagents were from Life Technologies, Rockville, Md.) containing 500 ug/ml G418 (Life Technologies) for 12 days. Cells resistant to G418 were trypsinized, pooled, and stained with FITC-conjugated human IgG, Fc fragment (FITC-hFc; Jackson ImmunoResearch Laboratories, West Grove, Pa.). Briefly, cells grown on 10 cm culture plates were washed once with Dulbecco's phosphate-buffered saline (PBS) without calcium chloride and magnesium chloride (Life Technologies). Two milliliters of 0.25% trypsin (Life Technologies) was added to each plate and incubated at 37° C. for 4-5 min. The plates were swirled until the cells detached from the plate. Four milliliters of culture medium was immediately added to each plate of the detached cells. The cells were then collected by centrifugation at 1,000×g for 4 minutes then resuspended in 4 ml of 2 ug/ml FITC-hFc diluted in culture medium. The cells were then placed on a platform shaker and stained for one hour at room temperature. To remove unbound FITC-hFc, the cells were washed twice with 8 ml PBS. Washed cells capable of binding FITC-hFc were measured by flow cytometry on a Moflo™ cell sorter (Cytomation; Fort Collins, Colo.). The FITC-hFc did not stain nontransfected parental CHO K1 cells but gave rise to a distribution of fluorescence in the G418-resistant, pTE158-transfected pool. The total pool of fluorescent cells from the G418-resistant population was collected by flow cytometry, expanded then analyzed by flow cytometry for expression of hFcγRI. Cells possessing the highest 15% fluorescence in this population were isolated, pooled, and expanded to yield a population of G418-resistant cells that expressed hFcγRI at high levels. This population of cells was named CHO K1-FcR and was used to isolate a clone that expressed the hFcγRI gene regulated by the TetR-$ER_{LBD}T2$ RFP after transfection with pTE313.

Example 3

Construction of CHO K1 Cell Lines with hFcγRI Expression Regulated by TetR-$ER_{LBD}T2$ CHO K1-FcR cells ($2 \times 10^6$ cells) were transfected with pTE313 using Lipofectamine™. The transfected cells were selected with 500 ug/ml G418 and 10 ug/ml blasticidin for 14 days to select for both plasmids, pTE158 and pTE313. Two days prior to analysis by flow-cytometry, cells were incubated in culture medium containing 200 nM tamoxifen (OHT) to stabilize the activity of TetR-$ER_{LBD}T2$ and repress expression of hFcgRI. The cells were stained with FITC-hFc and those cells possessing the lowest 2% fluorescence, indicating repression of hFcγRI expression, were collected to yield pool A1. This pool was then used as the source of cells for the two strategies outlined in FIG. 3.

Clones that expressed hFcγRI regulated by TetR-$ER_{LBD}T2$ were isolated by manipulating the activity of TetR-$ER_{LBD}T2$ by the presence or absence of doxycycline (Dox). One strategy involved the isolation of cells expressing high levels of hFcγRI in the presence of OHT and Dox, followed by the isolation of non-expressing cells in the presence of OHT without Dox. Alternatively, cells expressing low levels of hFcγRI in the presence of OHT without Dox were first isolated, then high expressing cells were isolated from this pool by the induction with Dox in the presence of OHT. Both strategies utilized a series of cell isolations under alternating inducing or repressing conditions, and a final isolation of single cells that expressed high levels of hFcγRI in the absence of both OHT and Dox (FIG. 3).

Pool A1 was expanded for 7 days in the presence of 200 nM OHT, then split into two dishes; one dish contained medium with 1 ug/ml Dox and the other did not. Cells were incubated for three days then stained with FITC-hFc to detect the presence of hFcγRI. The top 60% of hFcγRI-positive cells from the culture induced with 1 ug/ml Dox were isolated to yield pool B11, and cells with the lowest 30% fluorescence were isolated from cells grown in medium without Dox to yield pool B12. Pool B11 was grown in 200 nM tamoxifen without Dox and the cells with the lowest 1% fluorescence were collected to yield pool C11. Pool B12 was grown in 200 nM OHT and 1 ug/ml Dox, and the top 1% of hFcγRI-positive cells were collected as a pool to yield pool C12. Both pool C11 and pool C12 were then expanded in the absence of both OHT and Dox. Cells that expressed the highest levels of hFcγRI (top 1%) in the absence of OHT and Dox were then sorted onto 96 well plates at one cell per well. These cells should have low non-induced expression of hFcγRI and high levels of hFcγRI when induced by the removal of OHT as a consequence of alternating the isolation of induced or repressed hFcγRI expression.

After expansion, ten individual clones were characterized for the induction of hFcγRI, by withdrawal of OHT or addition of 1 ug/ml Dox, by immunostaining with FITC-hFc and analysis by flow cytometry. Analysis of one clone (D124 from pool C12) showed no detectable level of hFcγRI when OHT was present without Dox, whereas high levels of hFcγRI expression was observed in the absence of OHT and Dox. Furthermore, the addition of Dox at 1 μg/ml to cells grown in the presence of OHT also resulted in high levels of hFcγRI expression. The level of hFcγRI expression in this clone that resulted from induction by either removal of OHT or 1 ug/ml doxycycline, in the presence of OHT, were indistinguishable (FIG. 4).

Example 4

Construction of pTE528, pTE529, and pTE534

The phage P22 Arc repressor gene encodes a transcriptional repressor of 53 amino acids (M1 to A53 encoded by nucleotides 38,336 to 38,494 of the phage P22 genomic DNA (GenBank accession NC002371). Transcription repression mediated by Arc involves the sequential addition of dimers to operator half-sites. It was previously shown that a single chain dimer consisting of two Arc proteins connected by a 15 amino acid linker had higher affinity for arc operator DNA than the wildtype repressor (Robinson et al. (1996) Biochemistry 35:109-116). To take advantage of the higher affinity of the single chain dimer for operator DNA, a synthetic DNA was designed that encoded this single chain Arc dimer fused a His tag sequence consisting of 6 histidine residues. This 444 bp synthetic XhoI/NotI DNA fragment was cloned into pUC119 to yield pUC119-Arc2-His6 (Blueheron Technology Inc.). The Arc2 dimer gene was then excised from this plasmid and cloned into the Xho1 and Not1 sites of pRG985, such that expression of the Arc2 gene was dependent on the Ubc promoter/β-globin intron, to yield pTE528.

Figure 5:
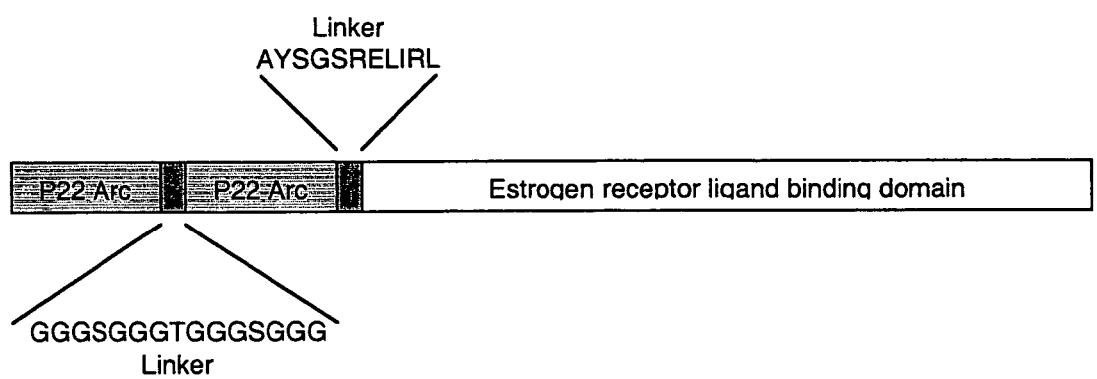
FIG. 5 is a schematic diagram of fusion protein Arc2-ER$_{LBD}$T2; with linkers GGGSGGGTGGGSGGG (SEQ ID NO:2) and AYSGSRELIRL (SEQ ID NO:1).

The Arc2-$ER_{LBD}T2$ fusion protein (FIG. 5) was constructed by ligating a 3361 bp BamH I fragment from pTE502, that contains the human $ER_{LBD}T2$ encoding DNA as described above, into the BamH I sites of pTE528 to yield pTE529. The resulting Arc2-$ER_{LBD}T2$ fusion protein had the same 11 amino acid linker (AYSGSRELIRL) (SEQ ID NO:1) between the Arc2 gene and the $ER_{LBD}T2$ gene as between TetR and $ER_{LBD}T2$ in TetR— $ER_{LBD}T^2$ (SEQ ID NO:3).

To change the Tet operators in CMV-MIE/TO promoter to Arc operators, encoded by base pairs 38,273 to 38,293 in the phage P22 genome (Genbank accession NC002371), pTE158 was used as a template to amplify a DNA fragment by PCR with the following primer set (5'-GAGTATTTA CGG-TAAACTGCCCACTT-3' (SEQ ID NO:4) and 5' GAGAGATCTGAGTCGACATAGTA-GAGTGCTTCTAT-CATGAATAGTAGAGTGCTTCTATCAT-GAGCTCTGCTTATATAGAC CTCCCA-3')(SEQ ID NO:5). The PCR product, encoding tandem Arc operators was digested with NdeI and SalI and cloned into the same sites in pTE158. The CMV-MIE/AO hybrid promoter has two tandem arc operators immediately downstream of the CMV-MIE promoter/enhancer (FIG. 6) (SEQ ID NO:6). Consequently, the Arc2-$ER_{LBD}T2$ transcriptional repressor will regulate transcription of hFcγRI from the CMV-MIE/AO promoter in pTE534.

Example 5

Construction of a CHO K1 Derivative that Expresses hFcγRI Driven by CMV-MIE/ArcO2 Promoter CHO K1 cells ($2 \times 10^6$) were transfected with pTE534 using Lipofectamine™ as described above. The cells were placed in the culture medium (10% fetal bovine serum, 90% Ham's F-12, 2 mM L-glutamine; all reagents were from Invitrogen Life Technologies, Carlsbad, Calif.) containing 400 ug/ml G418 (Invitrogen Life Technologies) for 12 days. Cells resistant to G418 were trypsinized, pooled, and stained with 2 μg/ml of FITC-conjugated human IgG, Fc fragment (FITC-hFc) as described above. The FITC-hFc did not stain non-transfected parental CHO K1 cells. Cells that expressed hFcγRI bound FITC-hFc and were isolated based on their fluorescence by flow cytometry on a Moflo™ cell sorter. Cells with the highest 3% fluorescence in this population were isolated, pooled, and expanded. This hFcγRI-positive pool was enriched by repeating the cell surface staining with FITC-hFc and sorting the top 30% most fluorescent cells in the population to yield pool B. Cells in pool B that were among the top 20% expressing hFcγRI were isolated to yield pool C. Pool C2 (CHOK1/pTE534) was used to generate inducible cell lines regulated by Arc-$ER_{LBD}T2$.

Example 6

Construction of CHO K1 Cell Lines with Arc-$ER_{LBD}T2$-Dependent hFcγRI Expression CHO K1/pTE534 cells ($2 \times 10^6$/dish) were transfected with either pRG985, an empty vector, or pTE529 using Lipofectamine™. The transfected cells were selected with 400 μg/ml G418 and 10 μg/ml puromycin in the absence of OHT for 14 days. The cells were stained with FITC-hFc as described above and analyzed by flow cytometry. The cells transfected with pRG985 were similar to parental cells and had similar hFcγRI staining profiles whether or not they were grown in the presence of OHT prior to analysis. In contrast, the expression hFcγRI expression in CHO K1/pTE534 cells transfected with pTE529 show marked response to the presence of OHT in the growth medium. In the absence of OHT in the growth medium, the majority of G418 and puromycin-resistant cells were positive for hFcγRI expression, and the top 30% hFcγRI-positive cells were sorted as a pool. This pool was expanded in the presence of OHT for 10 days, stained for hFcγRI expression and analyzed by flow cytometry. Over 70% of the cells in this pool did not express hFcγRI in the presence of OHT, and those cells expressing the lowest 30% were sorted as a pool. These cells were then expanded in the absence of OHT in the medium. Cells that expressed the highest levels of hFcγRI (top 1%) in the absence of OHT were sorted into a 96-well plate at one cell per well.

Clones showing tight regulation in response to the presence of OHT in the medium were further characterized by flow cytometry. The OHT-dependent regulation of hFcγRI expression in these clones was confirmed by immunostaining with FITC-hFc followed by flow cytometry analysis. No detectable level of hFcγRI was observed in one clone (C17) when OHT was present in the medium, whereas growth in the absence of OHT induced expression of hFcγRI in these clones (FIG. 7).

We claim:

1. An isolated nucleotide sequence encoding a regulatory fusion protein, wherein the fusion protein consists of two domains, wherein the two domains consist of
    (a) a modified ligand-binding domain of a human estrogen receptor consisting of amino acids N304 to V595 of SEQ ID NO:9 and having amino acids modifications G400V, M543A, and L544A that allow tamoxifen binding, and
    (b) a transcription blocking domain comprising a mutated restriction enzyme capable of binding but not cleaving DNA,
    wherein the fusion protein is stabilized and inhibits expression of a gene operably linked to an operator that is a recognition site for the mutated restriction enzyme in the presence of tamoxifen, but is destabilized and does not inhibit expression of the gene in the absence of tamoxifen.

2. An isolated nucleotide sequence encoding a regulatory fusion protein, wherein the fusion protein consists of two domains, wherein the two domains consist of:
    (a) a modified ligand-binding domain of a human estrogen receptor consisting of amino acids N304 to V595 of SEQ ID NO:9 and having amino acid modifications G400V, M543A, and L544A that allow tamoxifen binding; and
    (b) a bacterial or bacteriophage transcription blocking domain that binds a bacterial or bacteriophage operator, wherein the bacterial or bacteriophage transcriptional blocking domain consists of either
        (i) amino acids M1 to S207 of SEQ ID NO:8, or
        (ii) an Arc dimer comprising Arc monomers connected by a linker;
    wherein the fusion protein is stabilized and inhibits expression of a gene operably linked to the bacterial or bacteriophage operator in the presence of tamoxifen, but is destabilized and does not inhibit expression of the gene in the absence of tamoxifen.

3. A regulatory fusion protein consisting of two domains, wherein the two domains consist of:
    (a) a modified ligand-binding domain of a human estrogen receptor consisting of amino acids N304 to V595 of SEQ ID NO:9 and having amino acid modifications G400V, M543A, and L544A that allow tamoxifen binding, and
    (b) a bacterial or bacteriophage transcription blocking domain that binds a bacterial or bacteriophage operator, wherein the bacterial or bacteriophage transcription blocking domain consists of either
        (i) amino acids M1 to S207 of SEQ ID NO:8, or
        (ii) an Arc dimer comprising Arc monomers connected by a linker;
    wherein the fusion protein is stabilized and inhibits expression of a gene operably linked to the bacterial or bacteriophage operator in the presence of tamoxifen, but is destabilized and does not inhibit expression of the gene in the absence of tamoxifen, and wherein the fusion protein is encoded by the nucleotide sequence of claim 2.

4. A eukaryotic cell capable of inducible expression of a nucleotide sequence of interest, comprising
    (a) a promoter operably linked to the nucleotide sequence of interest and controlled by a bacterial or bacteriophage operator;
    (b) a nucleotide sequence encoding a regulatory fusion protein, wherein the regulatory fusion protein consists of two domains, wherein the two domains consist of
        (i) a modified ligand-binding domain of a human estrogen receptor consisting of amino acids N304 to V595 of SEQ ID NO:9 and having amino acid modifications G400V, M543A, and L544A that allow tamoxifen binding, and
        (ii) a bacterial or bacteriophage transcription blocking domain that binds a bacterial or bacteriophage operator, wherein the transcription blocking domain consists of either
            (1) amino acids M1 to S207 of SEQ ID NO:8, or
            (2) an Arc dimer comprising Arc monomers connected by a linker;
    wherein the fusion protein inhibits expression of the nucleotide sequence of interest by binding the bacterial or bacteriophage operator when the eukaryotic cell is exposed to tamoxifen, and wherein depletion of tamoxifen in the eukaryotic cell induces expression of the nucleotide sequence of interest.

5. The eukaryotic cell of claim 4, wherein the eukaryotic cell is selected from the group consisting of a COS, CHO, 293, BHK, and NS0 cell.

* * * * *

SEQUENCE LISTING

<160> NUMBER OF SEQ ID NOS: 6

<210> SEQ ID NO 1
<211> LENGTH: 11
<212> TYPE: PRT
<213> ORGANISM: homo sapiens

<400> SEQUENCE: 1

Ala Tyr Ser Gly Ser Arg Glu Leu Ile Arg Leu
 1               5                  10

<210> SEQ ID NO 2
<211> LENGTH: 15
<212> TYPE: DNA
<213> ORGANISM: homo sapiens

<400> SEQUENCE: 2
gggsgggtgg gsggg                                                    15

<210> SEQ ID NO 3
<211> LENGTH: 446
<212> TYPE: PRT
<213> ORGANISM: homo sapiens

<400> SEQUENCE: 3

Met Lys Gly Met Ser Lys Met Pro Gln Phe Asn Leu Arg Trp Pro Arg
 1               5                  10                  15

Glu Val Leu Asp Leu Val Arg Lys Val Ala Glu Asn Gly Arg Ser
                20                  25                  30

Val Asn Ser Glu Ile Tyr Gln Arg Val Met Glu Ser Phe Lys Lys Glu
             35                  40                  45

Gly Arg Ile Gly Ala Gly Gly Ser Gly Gly Gly Thr Gly Gly Gly
         50                  55                  60

Ser Gly Gly Gly Met Lys Gly Met Ser Lys Met Pro Gln Phe Asn Leu
65                  70                  75                  80

Arg Trp Pro Arg Glu Val Leu Asp Leu Val Arg Lys Val Ala Glu Glu
                 85                  90                  95

Asn Gly Arg Ser Val Asn Ser Glu Ile Tyr Gln Arg Val Met Glu Ser
            100                 105                 110

Phe Lys Lys Glu Gly Arg Ile Gly Ala Ala Tyr Ser Gly Ser Arg Glu
            115                 120                 125

Leu Ile Arg Leu Ser Ala Gly Asp Met Arg Ala Ala Asn Leu Trp Pro
        130                 135                 140

Ser Pro Leu Met Ile Lys Arg Ser Lys Lys Asn Ser Leu Ala Leu Ser
145                 150                 155                 160

Leu Thr Ala Asp Gln Met Val Ser Ala Leu Leu Asp Ala Glu Pro Pro
                165                 170                 175

Ile Leu Tyr Ser Glu Tyr Asp Pro Thr Arg Pro Phe Ser Glu Ala Ser
            180                 185                 190

Met Met Gly Leu Leu Thr Asn Leu Ala Asp Arg Glu Leu Val His Met
        195                 200                 205

Ile Asn Trp Ala Lys Arg Val Pro Gly Phe Val Asp Leu Thr Leu His
    210                 215                 220

Asp Gln Val His Leu Leu Glu Cys Ala Trp Leu Glu Ile Leu Met Ile
225                 230                 235                 240

Gly Leu Val Trp Arg Ser Met Glu His Pro Val Lys Leu Leu Phe Ala

```
                        245                 250                 255
Pro Asn Leu Leu Leu Asp Arg Asn Gln Gly Lys Cys Val Glu Gly Met
                260                 265                 270
Val Glu Ile Phe Asp Met Leu Leu Ala Thr Ser Ser Arg Phe Arg Met
            275                 280                 285
Met Asn Leu Gln Gly Glu Glu Phe Val Cys Leu Lys Ser Ile Ile Leu
        290                 295                 300
Leu Asn Ser Gly Val Tyr Thr Phe Leu Ser Ser Thr Leu Lys Ser Leu
305                 310                 315                 320
Glu Glu Lys Asp His Ile His Arg Val Leu Asp Lys Ile Thr Asp Thr
                325                 330                 335
Leu Ile His Leu Met Ala Lys Ala Gly Leu Thr Leu Gln Gln Gln His
                340                 345                 350
Gln Arg Leu Ala Gln Leu Leu Leu Ile Leu Ser His Ile Arg His Met
            355                 360                 365
Ser Asn Lys Gly Met Glu His Leu Tyr Ser Met Lys Cys Lys Asn Val
        370                 375                 380
Val Pro Leu Tyr Asp Leu Leu Leu Glu Ala Ala Asp Ala His Arg Leu
385                 390                 395                 400
His Ala Pro Thr Ser Arg Gly Gly Ala Ser Val Glu Glu Thr Asp Gln
                405                 410                 415
Ser His Leu Ala Thr Ala Gly Ser Thr Ser Ser His Ser Leu Gln Lys
                420                 425                 430
Tyr Tyr Ile Thr Gly Glu Ala Glu Gly Phe Pro Ala Thr Val
            435                 440                 445

<210> SEQ ID NO 4
<211> LENGTH: 26
<212> TYPE: DNA
<213> ORGANISM: homo sapiens

<400> SEQUENCE: 4
gagtatttac ggtaaactgc ccactt                                        26

<210> SEQ ID NO 5
<211> LENGTH: 86
<212> TYPE: DNA
<213> ORGANISM: homo sapiens

<400> SEQUENCE: 5
gagagatctg agtcgacata gtagagtgct tctatcatga atagtagagt gcttctatca   60
tgagctctgc ttatatagac ctccca                                        86

<210> SEQ ID NO 6
<211> LENGTH: 116
<212> TYPE: DNA
<213> ORGANISM: homo sapiens

<400> SEQUENCE: 6
tataagcaga gctcatgata gaatcactct actattcatg atagaagcac tctactatat   60
attcgtctcg agtactatct tagtgagatg ataagtacta tcttcgtgag atgata       116
```